United States Patent [19]

Franjac et al.

[11] Patent Number: 5,534,247
[45] Date of Patent: Jul. 9, 1996

[54] MASCARA COMPOSITION

[75] Inventors: David Franjac, Cordova; John Caradonna, Germantown, both of Tenn.

[73] Assignee: Maybelline Intermediate Co., Wilmington, Del.

[21] Appl. No.: 316,461

[22] Filed: Oct. 3, 1994

Related U.S. Application Data

[63] Continuation of Ser. No. 36,889, Mar. 25, 1993, abandoned.

[51] Int. Cl.$^6$ .................................................. A61K 7/032
[52] U.S. Cl. ...................... 424/707; 424/70.15; 424/63; 424/401; 132/218
[58] Field of Search .................. 424/70.7, 63, 401, 424/70.15; 132/218

[56] References Cited

U.S. PATENT DOCUMENTS

| | | | |
|---|---|---|---|
| 3,697,643 | 10/1972 | Shepherd et al. | 424/70.7 |
| 4,336,246 | 6/1982 | Leon-Pekarek | 424/63 |
| 4,369,037 | 1/1983 | Matsunaga et al. | 424/71 |
| 4,423,031 | 12/1983 | Murui et al. | 424/63 |
| 4,837,005 | 6/1989 | Brode, II et al. | 424/63 |
| 4,871,536 | 10/1989 | Arraudeau et al. | 424/63 |
| 4,988,502 | 1/1991 | Ounanian et al. | 424/63 |
| 5,013,543 | 5/1991 | Mercado et al. | 424/63 |
| 5,053,221 | 10/1991 | Robertson et al. | 424/63 |
| 5,389,363 | 2/1995 | Snyder et al. | 424/70.7 |

OTHER PUBLICATIONS

Product Label for Covergirl® Professional Mascara, Procter & Gamble, Jan. 1978.
Product Label for Lashfull Curvaceous™ Mascara, Revlon.

*Primary Examiner*—Amy Hulina
*Attorney, Agent, or Firm*—Sherman and Shalloway

[57] ABSTRACT

A mascara composition containing at least one curl retention additive to help enhance and sustain a curl along with a hair fixative resin designed to hold the eyelashes in a curled position by preventing the fixed eyelash hairs from being affected by humidity.

3 Claims, No Drawings

MASCARA COMPOSITION

This application is a continuation of application Ser. No. 08/036,889, filed Mar. 25, 1993, now abandoned.

FIELD OF THE INVENTION

The present invention relates to a mascara composition. More particularly, the present invention relates to a mascara composition which incorporates a hair fixative resin to hold eye lashes in a curled position and at least one curl retention additive to help sustain the curl.

BACKGROUND OF THE INVENTION

Mascara is a major cosmetic product, of significant importance to the cosmetic industry. Mascara is a composition utilized to enhance the beauty of a person's eyes by coating eyelashes, and in some cases, eyebrows, to make them more attractive by providing color and body. Mascaras usually contain lipids such as waxes, oils, or fats, pigments for color, water, thickeners, surface active agents, humectants and alcohol. Most current mascara products are designed to deposit and fix a mixture of waxes, colors and solvents onto the eyelashes by a variety of methods, typically by specially designed brushes. The deposited film adds color, and by virtue of the film deposited, make the lashes appear thicker and longer.

Over the years there have been a number of developments to improve the look and feel of mascara. Various film forming polymers have been used in mascara to improve the mascara's durability and resistance to water and tears.

U.S. Pat. No. 3,697,643 to Sheperd, et al. discloses the use of hydrophilic acrylate and methacrylate polymers in various cosmetics, for the purposes of, among other things, overcoming the tendency of mascara to run when wet, and, in other cosmetics such as hair sprays, to set hair of any type.

U.S. Pat. No. 4,423,031 to Murui, et al. discloses an aqueous emulsion of at least one copolymer of one or more $C_4$ to $C_{18}$ alkyl acrylates and one or more $C_1$ to $C_4$ alkyl methacrylates. This copolymer emulsion may be used instead of waxes, lipids or oils in mascara for water resistance, and resistance to rubbing.

U.S. Pat. No. 4,988,502 to Ounanian, et al. and U.S. Pat. No. 5,013,543 to Mercado, et al. use water soluble polyvinylpyrrolidone (PVP) and polyvinylacetate (PVA) as film forming resins in mascara instead of waxes, lipids, and oils.

U.S. Pat. No. 5,053,221 to Robertson et al. discloses a non-flaking, soapy water removable mascara composition which is an aqueous dispersion of an anionic polyester polymer derived from an aromatic dicarboxylic acid and aliphatic or cycloaliphatic glycol residues, in addition to microsphere particles.

As far as the present inventors are aware, neither these nor other previous mascara preparations are designed to or include any ingredient for holding the eye lashes in a curled position and retaining that curl.

SUMMARY OF THE INVENTION

This invention provides for a mascara composition which contains a hair fixative resin, designed to hold the eye lashes in a curled position and a curl retention additive to help sustain the curl by preventing the fixed eye lash hairs from being affected by humidity. The hair fixative resin is at least one hair fixative polymer or copolymer, and the curl retention additive is at least one quaternized compound.

The invention mascara composition may further include an effective amount of conventional mascara composition additives, including:

at least one lipid selected from oils, waxes, fats, and combinations thereof;

humectant;

pigment;

surface active agent;

thickener;

low molecular weight alcohol having from 1 to 7 carbon atoms; and water.

Other known ingredients that may be used in this mascara composition include effective amounts of emulsifiers, emollients, preservatives, pH adjusters, moisturizing agents, sequestering agents, and perfumes.

DETAILED DESCRIPTION AND PREFERRED EMBODIMENTS

The hair fixative resin which may be used in this invention includes any of the known hair fixative resins which are cosmetically acceptable for use in contact with the eyes. Preferred as the hair fixture resins are water-insoluble or water dispersible polymers and copolymers (hereinafter referred to broadly as polymers) which may be used to preferably form oil in water emulsions. These polymers should have a fast setting speed (e.g. about 60 to about 300 seconds), i.e. a fast drying time—and should form a hard, clear, flexible film that adheres gently to the lashes. The polymers should also have an excellent adhesiveness to human skin and hair and should have excellent water resistant properties, although the preferred polymers are capable of being removable with soap and water. Generally, polymers and copolymers which are useable in this invention include poly(meth)acrylates, polyamides, polyesters, polystyrenes, polyvinyl pyrrolidones, polyvinylmethyl ethers, polyvinyl alcohols, polyvinyl acetates, polyacryl compounds, such as acrylic or methacrylic and polymers, basic polymers of esters of acrylic acid or methacrylic acid with amino alcohols and the salts or quaternization products thereof, inclusive of copolymers of the foregoing classes of polymers. For example, the following polymers and copolymers may be mentioned:

(a) acrylic/acrylate copolymers;

(b) octylacrylamide/acrylates/butylaminoethyl methacrylate copolymers;

(c) vinylpyrrolidone/dimethylaminoethyl methacrylate copolymers;

(d) polyamide resins;

(e) diglycol/cyclohexanedimethanol/isophthalates/sulfoisophthalates;

(f) sodium polystyrene sulfonates;

(g) vinylcaprolactam/polyvinylpyrrolidone/dimethylaminoethyl/methacrylate copolymers;

(h) polyvinyl methyl ether/maleic anhydride (PVM/MA) copolymers;

(i) polyvinyl pyrrolidone/vinyl alcohol (PVP/VA) copolymers;

(j) vinyl alcohol/crotonate copolymers;

A preferred polymer is an anionic polyester polymer which has the structural formula (I) shown below, such as the above-mentioned polyester containing units of diglycolcyclohexanedimethanol-isophthalates-sulfoisophthalates. These preferred polyester polymers (I) are available from Eastman Chemicals under the general product designation EASTMAN AQ polymers. These polyester polymers are reportedly relatively high molecular weight, amorphous polyesters that disperse directly in water without the assistance of organic cosolvents, surfactants, or amines. It is reported that this water-dispersibility is attributable, in large part, to the presence of ionic substituents attached to the polymer chain (see Formula I below). It is also reported that some of the aromatic dicarboxylic acid units in EASTMAN AQ polymer chains have sodiosulfo ($SO_3$—Na+) substituents; although only two are shown in Formula I below, on the average, there are five to eight ionic sodiosulfo substituents per molecule.

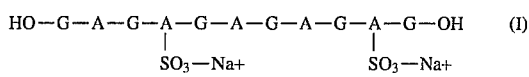

In Formula I, A is an aromatic dicarboxylic acid moiety, G is an aliphatic or cycloaliphatic glycol residue, and —OH are hydroxy end groups.

Suitable polyester polymers are commercially available under the product designations AQ29S, AQ38S and AQ55S from Eastman Chemical Products, Inc. The polymers obtained in the solid form are indicated by the letter "S" in the product designation.

AQ29S is reported to have the specifications: (1) approximate molecular weight, Mn, 16,000; (2) hydroxyl number, <10; (3) acid number, <2; (4) Tg, C., 29; and (5) melt viscosity at 200° C. (392° F.), 2000 poise, as measured with a Sieglaff-McKelvey Capillary Rheometer, 100 $sec^{-1}$ shear rate.

AQ38S is reported to have the specifications: (1) approximate molecular weight, Mn, 14,000; (2) hydroxyl number, <10; (3) acid number, <2; (4) Tg, C., 38; (5) melt viscosity at 200° C. (392° F.), 9700 poise as measured with a Sieglaff-McKelvey Capillary Rheometer, 100 $sec^{-1}$ shear rate.

AQ55S is reported to have the specifications: (1) approximate molecular weight, Mn, 14,000; (2) hydroxyl number, 10; (3) acid number, <2; (4) Tg. °C., 55; (5) melt viscosity at 200° C. (392° F.), 42,000 poise, as measured with a Sieglaff-McKelvey Capillary Rheometer, 100 $sec^{-1}$ shear rate.

All of these polymers are believed to have structural units of diglycol-cyclohexanedimethanol-isophthalates-sulfoisophthalates. Dispersions having different percent solids may be obtained from Kodak Chemical Products, Inc.

A dispersion of AQ55S having a solids content (as measured with 1 g of dispersion at 105° C. for 1 hour) of about 30 to about 36% by weight of the dispersion and a pH of 5.6 to 6.6 is preferred.

Further information about the Eastman AQ polymers may be obtained from the Eastman Chemicals product brochure, titled, "EASTMAN AQ® POLYMERS Properties and Applications", Publication No. GN-389, March 1989, the disclosure of which is incorporated herein by reference thereto. See also the aforementioned U.S. Pat. No. 5,053,221 (Robertson, et al.).

For the acrylate and methacrylates polymers and copolymers that may be used, alkyl acrylates having from $C_4$ to $C_{18}$ alkyl groups, preferably from $C_4$ to $C_8$ alkyl groups, in the ester portion, and one or more alkyl methacrylates having from $C_1$ to $C_4$ groups in the ester portion, are preferred.

The alkyl acrylates used in the present invention include, for example, butyl acrylate (BA) isobutyl acrylate (IBA), hexyl acrylates (HA), 2-ethylhexyl acrylate (2EHA) and the like. The use of 2-ethylhexyl acrylate or mixtures thereof with the other alkyl acrylates having from $C_4$ to $C_8$ alkyl groups is most preferable. In the case where the carbon atoms of the alkyl ester portion of the alkyl acrylate which is used alone or together with the other alkyl acrylates are 3 or less, the water resistant property of the copolymer films becomes poor, so that good eye makeup preparations cannot be obtained when such copolymer emulsion is incorporated into the eye makeup preparations. Conversely, in the case where there are 19 or more carbon atoms in the alkyl ester portion of the alkyl acrylate, the reactivity of the alkyl acrylates in an emulsion polymerization is unpreferably low. Since a copolymer emulsion containing alkyl acrylates having $C_9$ or more alkyl groups in the ester portion has an unpleasant odor (the removal of odor tends to be difficult when the molecular weight of the monomer becomes large), the incorporation of such copolymer emulsion into the makeup preparations is somewhat limited.

Alkyl methacrylates used, together with the alkyl acrylates, in the production of the aqueous copolymer emulsion of the present invention include those which have a minimum film-forming temperature (MFT) (represented by a glass transition temperature Tg) of 0° C. or more when they are polymerized alone. Examples of such alkyl methacrylates are methyl methacrylate (MMA), ethyl methacrylate (EMA), butyl methacrylate (BMA) and the like. Other comonomers which are copolymerizable with the alkyl acrylates and which have a MFT (Tg) of 0° C. or more may be used, together with the alkyl acrylates, in the production of the aqueous emulsion of the present invention. Other acrylate or methacrylate monomers that may be used to impart hydrophilic properties are hydroxyalkyl monoacrylates or methacrylates such as 2-hydroxyethyl acrylate, 2-hydroxyethyl methacrylate, diethylene glycol monoacrylate, diethylene glycol monomethacrylate, hydroxypropyl acrylates and methacrylates, e.g. 2-hydroxypropyl acrylate, 2-hydroxypropyl methacrylate, 3-hydroxypropyl acrylate, 3-hydroxypropyl methacrylate, tetraethylene glycol monomethacrylate, pentaethylene glycol monomethacrylate, dipropylene glycol monomethacrylate, and dipropylene glycol monoacrylate. Acrylamide, methacrylamide, diacetone acrylamide, methylolacrylamide and methylol methacrylamide also are useful hydrophylic monomers. The most preferred monomer is 2-hydroxyethyl methacrylate and the next most preferred monomer is 2-hydroxyethyl acrylate.

The copolymerization ratio of the alkyl acrylates to the alkyl methacrylates may be varied depending on the kinds of acrylates and methacrylates, the types of eye makeup preparations, the kinds and amounts of the other components incorporated into the eye makeup preparations (e.g. pigments, oils). However, generally speaking, the preferable ratio (by weight) of the alkyl acrylates to the alkyl methacrylates is within the range of from 3/7 to 8/2 and, more preferably, the range of from 5/5 to 7/3. This range approximately corresponds to the range of a MFT (Tg) of the copolymer of from 50° C. to −55° C., and, more preferably, of from 10° C. to −10° C. The solid content of the aqueous solid copolymer emulsions is preferably within the range of from 20 to 50% by weight, based on the total weight of the eye makeup preparation. The preferable content of the solid copolymer in the preparation is within the range of from 10 to 25% by weight.

The above-mentioned aqueous emulsions can be prepared according to any conventional emulsion polymerization techniques. A small amount of carboxyl-containing monomers (e.g. acrylic acids, methacrylic acids) may be optionally used, as comonomers, in addition to the alkyl acrylates and the alkyl methacrylates.

The hair fixative resins described above may be used individually or in mixtures of two or more of such resins.

The mascara composition preferably contains from about 1 to about 20% by weight, more preferably from about 4 to 18% by weight of the hair fixative resin.

The purpose of the curl retention additives is to help retain the curl that has been shaped and formed. The curl retentive additives should act as a conditioning agent, and are believed to function by binding to the keratin in the eye lash. They also serve to increase viscosity of the compositions. Suitable quaternized compounds include:

(a) diquaternary polydimethylsiloxane;

(b) stearalkonium chloride;

(c) quaternized protein;

(d) quaternized chitosan;

(e) panthenyl hydroxypropyl steardimonium chloride, (f) polyquaternium 11 (quaternized ammonium polymer formed by reacting dimethyl sulfate and a copolymer of vinyl pyrrolidone and dimethylaminomethylacrylate);

(g) polyquaternium 28; and combinations thereof.

These compounds are commercially available and are described in more detail in the CTFA, Cosmetic Ingredient Dictionary, Third Edition, and Third Addition Supplement, both of which are incorporated herein by reference thereto.

The mascara composition preferably contains from about 0.01 to about 2% by weight, more preferably from about 0.05 to 1.6% by weight of the curl retention additive.

The mascara composition preferably contains from about 30% to about 60% water. Of course, less water may be used in the mascara composition, depending on whether the mascara composition is in the form of a cake or powder, a dispersion, an oil in water (o/w) emulsion or a water in oil (w/o) emulsion. It is preferred that the mascara is in the form of an oil in water emulsion for ease of manufacture and for ease of application, usually by means of a suitable applicator brush.

Additionally, the mascara composition further comprises an effective amount, usually from about 1 to about 30% by weight, of at least one lipid selected from the group consisting of oils, waxes, fats, and combinations thereof. In this composition, waxes are the preferred lipids.

As a general rule, the waxes chosen have a melting point between 60° and 100° C. and a needle penetration, as measured according to the American standard ASTM D5 or according to the French standard NFT 004 of 3 to 40 at 25° C. The principle of the measurement of the needle penetration according to the standards ASTM D5 and NFT 004 consists in measuring the depth, expressed in tenths of a millimeter, to which a standard needle (weighing 2.5 g and placed in a needle holder weighing 47.5 g, i.e. a total of 50 g) penetrates when placed on the wax for 5 seconds.

The waxes employed according to the invention may be chosen from animal waxes, plant waxes, mineral waxes, synthetic waxes, and the various fractions of natural waxes. All these waxes should have the two characteristics; i.e. melting points and needle penetration, indicated above.

Among the animal waxes, there may be mentioned beeswaxes, spermaceti, lanolin waxes, lard, and Chinese insect waxes.

Among the plant waxes there may be mentioned carnauba, candelilla and ouricury waxes, cork fiber waxes, sugar cane waxes, and Japan waxes.

Among the mineral waxes there may be mentioned paraffins, microcrystalline waxes, montan waxes, petrolatum waxes, and ozokerites.

In the case of synthetic waxes, there may be mentioned polyethylene waxes, the waxes produced by the Fischer-Tropsch synthesis, and waxy copolymers, as well as their esters.

The waxes which can be employed according to the present invention are preferably solid and rigid at a temperature below 50° C.

Other oils and fats that may be used in the mascara composition include mineral oil, hydrogenated fish oils, squalane, isopropyl myristate, liquid paraffin, vegetable oils, lanolin isolates, almond oil, oleic acid, stearic acid, and combinations thereof.

The composition preferably contains from about 1 to about 8% by weight of a humectant.

The humectants used in the present invention may be any of the humectants which are incorporated into conventional eye makeup preparations. Examples of such humectants include glycerin, sorbitol, propylene glycol, glycol dibehenate, glycol dioctanoate, glycol distearate, glycol hydroxystearate, glycol oleate, glycol ricinoleate, glycol salicyate, glycol stearate, glycol stearate DSE, sodium PCA and mixtures thereof.

The mascara compositions according to the present invention preferably contains from about 1 to about 15% weight of a pigment of the type usually used in mascara compositions.

The pigments which can be employed in accordance with the invention are chosen from inorganic pigments approved for eye area use by the Food and Drug Administration.

Examples of finely divided inorganic pigments include bismuth oxychloride, iron oxide black, iron oxide yellow, iron oxide red, zinc oxide, kaolin, carmine, chromium hydroxide, green chromium oxide green, manganese violet, titanium oxide, titanium dioxide, ferric blue, chromium hydrate, and combinations thereof.

When in emulsion form, the mascara compositions preferably contain from about 1 to about 6% by weight of surface-active agents which are well known in the state of the art.

A particularly preferred embodiment consists in preparing anionic or nonionic emulsions by using anionic or nonionic surface-active agents in proportions which are preferably between about 2 and about 30% by weight relative to the total weight of the composition.

Among the anionic surface-active agents which may be used by themselves or mixed, there may be mentioned, in particular, the alkali metal salts, the ammonium salts, the amine salts or the amino-alcohol salts of the following compounds:

alkylsulphates, alkyl ether sulphates, alkylamidosulphates alkylamide ether sulphates, alkylaryl polyether sulphates and monoglyceride sulphates, alkylsulphonates, alkylamide sulphonates, alkylaryl sulphonates, α-olefin sulphonates and paraffin sulphonates, alkylsulphosuccinates, alkyl ether sulphosuccinates, and alkylamidosulphosuccinates, alkylsulphoacetates, alkylpolyglycerol carboxylates, alkyl phosphates/alkyl ether phosphates, alkylamidopolypeptidates, alkylisethionates, and alkyltaurates.

The alkyl radical in all these compounds generally denotes a chain containing 12 to 18 carbon atoms.

Other anionic surface-active agents include salts of fatty acids such as oleic, ricinoleic, palmitic and stearic acids, copra oil acids or hydrogenated copra oil acids and especially amine salts such as amine stearates.

There may also be mentioned: the acyl lactylates in which the acyl radical contains from 8 to 20 carbon atoms, and the polyglycol ether carboxylic acids corresponding to the formula $$Alk-(OCH_2-CH_2)_n-OCH_2-COOH$$

in acid or salt form, in which the substituent Alk corresponds to a linear chain containing from 12 to 18 carbon atoms and in which n is an integer from 5 to 15.

Among the nonionic surfactants which may be employed by themselves or mixed, there may be mentioned in particular; polyethoxylated, polypropoxylated or polyglycerolated (including mixtures thereof) alcohols, alkylphenols and fatty acids containing a fatty chain with from about 8 to 18 carbon atoms. There may also be mentioned copolymers of ethylene propylene oxides, ethylene oxide and propylene oxide condensates with fatty alcohols, polyethoxylated fatty amides, polyethoxylated fatty amines, ethanolamides, glycol fatty acid esters, sorbitan fatty acid esters which are oxyethylenated or otherwise, sucrose fatty acid esters which may be oxyethylenated, polyethylene glycol fatty acid esters, phosphoric triesters, and fatty acid esters of glucose derivatives.

Other compounds forming part of this class are: the products of condensation of a monoalcohol, an α-diol, an alkylphenol, an amide or a diglycolamide with a glycidol or a glycidol precursor such as:

$$R_4-CHOH-CH_2-O-(CH_2-CHOH-CH_2-O-)_pH$$

in which $R_4$ denotes an aliphatic, alicyclic or arylaliphatic radical preferably containing from 7 to 21 carbon atoms and their mixtures, the aliphatic chains being capable of containing ether, thioether or hydroxymethylene groups and in which p is from 1 to 10 inclusive, such as described in French Patent 2,091,516. Also useful are compounds corresponding to the formula:

$$R_5O-C_2H_3O-(CH_2-OH)_qH$$

in which $R_5$ denotes an alkyl, alkenyl or alkylaryl radical and q has a statistical value from 1 to 10 inclusive, such as described in French Patent 1,477,048 and compounds corresponding to the formula:

$$R_6-CONH-CH_2-CH_2O-CH_2-CH_2-O-(CH_2-CHOH-CH_2-O-)_rH$$

in which $R_6$ denotes a radical or a mixture of straight chain or branched, saturated or unsaturated aliphatic radicals which may optionally contain one or more hydroxyl group(s), containing from 8 to 30 carbon atoms, of natural or synthetic origin, r denotes an integer or decimal number from 1 to 5 and denotes the average degree of condensation, such as are described in French Patent 2,378,763.

The nonionic emulsifiers may be, for example, a mixture of oil and/or a fatty alcohol, or polyethoxylated or polyglycerolated alcohols such as polyethoxylated stearyl or ceteraryl alcohols.

Thickeners may also be added to the mascara composition, usually in amounts of from about 0.1 to about 2% by weight of the composition. The thickeners that are employed may be natural or synthetic. Natural thickeners include gum arabic, guar gum, and carob gum. Synthetic thickeners include hydroxyethyl cellulose, carboxymethylcellulose, starch derivatives, cellulose ether derivatives containing quaternary ammonium groups, cationic polysaccharides, acrylic or methacrylic polymer salts, polyenes, and polysiloxanes, and various combinations thereof. Thickening of the mascara composition may also be produced by a mixture of polyethylene glycol and polyethylene glycol stearate, a mixture of polyethylene glycol and polyethylene glycol distearate, a mixture of phosphoric esters and fatty amides, etc.

A moisturizing agent may preferably also be added to the mascara usually in an amount of from about 0.01% to about 1% by weight of the composition. Examples of the moisturizing agent which may be used include hydrolyzed elastin, hydrolyzed keratin, hydrolyzed silk, hydrolyzed animal protein, hydrolyzed milk protein, hydrolyzed mucopolysaccharides, potassium coco-hydrolyzed animal protein, myristoyl hydrolyzed animal protein, and mixtures thereof.

The mascara compositions also may include a low molecular weight alcohol having from 1 to about 7 carbon atoms, preferably 2 to 5 carbon atoms, especially 2 to 3 carbon atoms, usually in an amount from about 1 to about 20% by weight of the mascara composition.

The composition may also contain a sequestering agent in a concentration of between about 0.01% and about 0.1% by weight of the composition. The sequestering agents are preferably disodium EDTA and trisodium EDTA.

In addition to the above-mentioned ingredients, the mascara may contain other optional ingredients such as preservatives, such as imizadolidinyl urea, diazolidinyl urea, methylparaben, ethylparaben, propylparaben, butylparaben, sodium dehydroacetate, sorbic acid, sodium benzoate; perfumes; neutralizing agents, such as sodium bicarbonate, aqueous ammonia and the like, inorganic dispersing agents such as sodium hexamataphosphate, sodium tripolyphosphate, mixtures thereof; and the like.

The mascara composition should have a pH in the range of 3–11, preferably 6–8, and more preferably 7.2–7.8. The pH of the composition can be adjusted by the addition of sodium hydroxide, and various buffers such as, for example, sodium bicarbonate.

It is preferred that the mascara composition have a melt viscosity of about 2,000 to about 42,000 poise as measured with a Sieglaff McKelvey Capillary Rheometer 100 sec$^{-1}$ shear rate. The desired viscosity may be reached by the use of a colloid mill to further grind the mascara composition after the additions of the polymer to the mascara composition.

The mascara composition may be applied to the eyelashes by a variety of means, such as by a blotter, or a finger, but the preferred mode is by a brush, and an even more preferred mode is by a curved brush which will assist in curling the eyelashes as the mascara is applied. The radius of the curved brush lends itself to a more pronounced curling action as the brush with the product is passed through the lashes.

After the application of the mascara, the curled look of the eyelashes lasts about eight hours.

The following examples are given to illustrate the scope of the present invention. Because these examples are given for illustrative purposes only, the invention should not be inferred to be limited to these examples.

EXAMPLE I

An oil in water (o/w) emulsion mascara having the following composition is prepared as discussed below:

| | |
|---|---|
| Beeswax | 6.00 |
| Ceresin wax | 3.00 |
| Carnauba wax | 3.50 |
| Stearic acid | 3.00 |
| Glyceryl monostearate | 2.50 |
| Butylparaben | 0.05 |
| Water | 44.30 |
| Polyquaternium-4 | 0.50 |
| Triethanolamine | 2.25 |
| Octylacrylamide/Acrylates/Butylaminoethyl Methacrylate Copolymer | 3.00 |
| Methylparaben | 0.45 |
| Ammonium acrylates copolymer (and) propylene glycol (and) Potassium octoxynol-12 phosphate (and) Nonoxynol-10 | 10.00 |
| Black iron oxide | 10.00 |
| Polyquaternium-29 | 0.75 |
| Panthenyl hydroxypropyl steardimonium chloride | 0.50 |
| Quaternium-15 | 0.20 |
| Ethanol | 10.00 |

The beeswax, ceresin wax, carnauba wax, stearic acid, and glyceryl monostearate are heated to 80° C. The triethanolamine, butylparaben and methylparaben are dispersed or dissolved in the deionized water and ethanol. This water mixture, which is also heated to 80° C., is gradually added into the oil mixture with stirring and is uniformly emulsified therein. The black iron oxide is uniformly dispersed in the emulsion.

The octylacrylamide/acrylates/butylaminoethyl methacrylate copolymer, and the ammonium acrylates copolymer are each separately prepared or formed in deionized water. These copolymers are added and uniformly mixed, along with polyquaternium 4, quaternium 15, polyquaternium 29 and panthenyl hydroxypropyl steardimonium chloride, into the mixture. The pH is adjusted to between 7.2–7.8.

EXAMPLE II

An oil in water (o/w) emulsion mascara having the following composition is prepared as discussed below:

| | |
|---|---|
| Beeswax | 6.00 |
| Ceresin wax | 3.00 |
| Carnauba wax | 3.50 |
| Stearic acid | 3.00 |
| Glyceryl monostearate | 2.50 |
| Butylparaben | 0.05 |
| Iron oxide | 10.00 |
| Water | 46.80 |
| Triethanolamine | 2.25 |
| Polysorbate 20 | 0.50 |
| Polyquaternium-11 | 4.00 |
| Methylparaben | 0.45 |
| Acrylates Copolymer | 10.00 |
| Polyquaternium-29 | 0.50 |
| Panthenyl hydroxypropyl steardimonium chloride | 0.50 |
| Quaternium-15 | 0.20 |
| Ethanol | 7.50 |

The beeswax, ceresin wax, carnauba wax, stearic acid, polysorbate 20 and glyceryl monostearate are heated to 80° C. The triethanolamine, butylparaben, and methylparaben are dispersed or dissolved in the deionized water and ethanol. This water mixture, which is also heated to 80° C., is gradually added into the oil mixture with stirring and is uniformly emulsified therein. The black iron oxide is uniformly dispersed in the emulsion.

The acrylates copolymer is formed in deionized water. This copolymer is added and uniformly mixed along with polyquaternium- 11, quaternium 15, polyquaternium 29 and panthenyl hydroxypropyl steardimonium chloride, into the mixture. The pH is adjusted to between 7.2–7.8.

EXAMPLE III

An oil in water (o/w) emulsion mascara having the following composition is prepared as discussed below:

| | |
|---|---|
| Beeswax | 7.00 |
| Ceresin wax | 2.50 |
| Carnauba wax | 3.50 |
| Stearic acid | 3.00 |
| Glyceryl monostearate | 2.50 |
| Butylparaben | 0.05 |
| Iron oxide | 10.00 |
| PVP/Dimethylaminoethyl methacrylate copolymer | 2.50 |
| Water | 44.60 |
| Triethanolamine | 2.00 |
| Polyquaternium-11 | 1.50 |
| Methylparaben | 0.45 |
| Acrylates copolymer | 10.00 |
| Quaternium-15 | 0.20 |
| Ethanol | 10.00 |
| Panthenyl hydroxypropyl steardimonium chloride | 0.20 |

The beeswax, ceresin wax, carnauba wax, stearic acid, polysorbate 20, and glyceryl monostearate are heated to 80° C. The triethanolamine, butylparaben and methylparaben are dispersed or dissolved in the deionized water and ethanol. This water mixture, which is also heated to 80° C., is gradually added into the oil mixture, with stirring, and is uniformly emulsified therein. The black iron oxide is uniformly dispersed in the emulsion.

The PVP/dimethylaminoethyl methacrylate copolymer and the acrylates copolymer are each separately prepared or formed in deionized water. These copolymers are added and uniformly mixed along with polyquaternium-11, quaternium-15, and panthenyl hydroxypropyl steardimonium chloride into the mixture. The pH is adjusted to between 7.2–7.8.

EXAMPLE IV

An oil in water (o/w) emulsion mascara having the following composition is prepared as discussed below:

| | |
|---|---|
| Beeswax | 7.50 |
| Carnauba wax | 3.00 |
| Glyceryl monostearate | 3.00 |
| Stearic acid | 2.50 |
| Butylparaben | 0.05 |
| Black 3190 | 12.00 |
| Water | 48.70 |
| Triethanolamine | 1.70 |
| Propylene glycol | 1.00 |
| Diglycol/Cyclohexanedimethanol/Isophthalates/Sulfoisophthalates copolymer | 6.25 |
| PVP/VA copolymer | 5.30 |
| Hydroxyethylcellulose | 0.15 |
| Methylparaben | 0.45 |
| Quaternium-15 | 0.20 |
| Ethanol | 8.00 |
| Polyquaternium-29 | 0.10 |
| Panthenyl hydroxypropyl steardimonium chloride | 0.10 |

The beeswax, ceresin wax, carnauba wax, stearic acid, and glyceryl monostearate are heated to 80° C. The triethanolamine, butylparaben, methylparaben, propylene glycol, and hydroxyethylcellulose are dispersed or dissolved in the deionized water and ethanol. This water mixture, which is also heated to 80° C. is gradually added in the oil mixture with stirring and is uniformly emulsified therein. The black iron oxide is uniformly dispersed in the emulsion.

The PVP/VA copolymer and the diglycol/cyclohexane dimethanol/isophthalates/sulfoisophthalates copolymer are each separately prepared or formed in deionized water. These copolymers are added and uniformly mixed, along with polyquaternium 29, quaternium 15, and panthenyl hydroxypropyl steardimonium chloride, into the mixture. The pH is adjusted to between 7.2–7.8.

What is claimed is:

1. A mascara composition in the form of an oil-in-water emulsion comprising:

from about 10% to about 15% by weight of a hair fixative resin comprising a mixture of polyvinylpyrrolidone/vinyl acetate copolymer and diglycol/cyclohexanedimethanol/isophthalate/sulfoisophthalate copolymer;

from about 14% to about 20% by weight of lipid comprising at least one wax;

from about 1% to about 3% by weight of a humectant comprising propylene glycol;

from about 10% to about 15% by weight of pigment;

from about 2% to about 6% by weight of surface active agent emulsifier;

from about 0.5% to about 2% by weight of thickener comprising hydroxyethyl cellulose;

from about 0.05% to about 1.6% by weight of a curl retention additive comprising a mixture of Polyquaternium 29 and panthenyl hydroxypropyl steardimonium chloride;

from about 8% to about 10% by weight ethanol; and from about 40% to about 50% by weight of water.

2. A method for curling eyelashes and sustaining the curl so formed, comprising:

applying to the eyelashes with a curved brush having deposited thereon for transfer to the eyelashes a mascara composition comprising a mixture of polyvinyl pyrrolidone/vinyl acetate copolymer and diglycol/cyclohexanedimethanol/isophthalate/sulfoisophthalate copolymer as a hair fixative resin in an amount effective to hold the eyelashes in a curled position formed by the curved brush, and a curl retention additive comprising a mixture of Polyquaternium 29 and panthenyl hydroxypropyl steardimonium chloride in an amount effective to sustain the curl, thereby transferring the mascara composition to the eyelashes whereby the curls imparted to the eyelashes may be sustained for up to about eight hours.

3. A method for simultaneously mechanically forming and chemically sustaining curled eyelashes, comprising:

depositing on a curved brush a mascara composition comprising a mixture of polyvinyl pyrrolidone/vinyl acetate copolymer and diglycol/cyclohexanedimethanol/isophthalate/sulfoisophthalate copolymer in an amount effective to hold eyelashes in a curled position and a curl retention additive comprising a mixture of Polyquaternium 29 and penthenyl hydroxypropyl steardimonium chloride in an amount effective to sustain the curl, and, curling the eyelashes with the curved brush while the mascara on the brush is applied to the eyelashes, whereby curls formed by the brush will be held in place and sustained for up to about eight hours.

* * * * *